United States Patent
Fasanella

(10) Patent No.: US 6,637,278 B1
(45) Date of Patent: Oct. 28, 2003

(54) MEASURING SYSTEM FOR DETERMINING THE SURFACE LINE OF A BODY

(75) Inventor: Piero Fasanella, Brüttisellen (CH)

(73) Assignee: Idiag, Volkeiswil (CH)

( * ) Notice: Subject to any disclaimer, the term of this patent is extended or adjusted under 35 U.S.C. 154(b) by 0 days.

(21) Appl. No.: 09/807,935

(22) PCT Filed: Nov. 4, 1999

(86) PCT No.: PCT/CH98/00467

§ 371 (c)(1),
(2), (4) Date: Aug. 2, 2001

(87) PCT Pub. No.: WO00/25674

PCT Pub. Date: May 11, 2000

(Under 37 CFR 1.47)

(51) Int. Cl.[7] .................. A61B 5/103; A61B 5/107; G01B 5/00; G01B 5/20; G01B 5/24
(52) U.S. Cl. .................. 73/865.8; 73/104; 33/773; 33/775; 33/512; 600/587
(58) Field of Search .................. 73/104, 865.8, 73/865.4; 33/773, 775, 774, 779, 780, 532, 511, 512; 600/587, 594, 595; 702/155, 158, 163, 164, 167, 168

(56) References Cited

U.S. PATENT DOCUMENTS

| | | | | |
|---|---|---|---|---|
| 5,107,598 A | * | 4/1992 | Woznow et al. | 73/146 X |
| 5,291,900 A | * | 3/1994 | Lowenstein | 33/773 X |
| 5,331,578 A | * | 7/1994 | Stieler | 73/866.5 X |
| 5,351,408 A | * | 10/1994 | Street | 33/512 |
| 6,050,960 A | * | 4/2000 | Ferzli | 600/587 |

FOREIGN PATENT DOCUMENTS

| | | | | |
|---|---|---|---|---|
| DE | 4090228 | * | 5/1994 | A61B/5/103 |
| DE | 4402562 | * | 8/1995 | A61B/5/107 |
| EP | 487339 | * | 5/1992 | 600/443 |
| FR | 2529776 | * | 1/1984 | G01B/5/20 |
| GB | 2045938 | * | 11/1980 | 33/561 |

* cited by examiner

Primary Examiner—Thomas P. Noland
(74) Attorney, Agent, or Firm—Notaro & Michalos P.C.

(57) ABSTRACT

A measuring system has a freely movable measuring instrument and a computer for processing the measured data. Two measuring devices are in the measuring instrument, each with two acceleration sensors. Two of the sensor each in a common plane and the two measuring planes are at right angles to one another. A measuring wheel is in the measuring instrument for acquiring the length of the displacement path of the measuring instrument. The measuring instrument acquires the shape and length of a surface line of a body and its representation in two spatial planes with a measuring range from 0 to 360° in one plane. Input elements and a display arrangement on the measuring instrument serve to simplify the measuring process and permit direct control and monitoring of the measuring process.

11 Claims, 4 Drawing Sheets

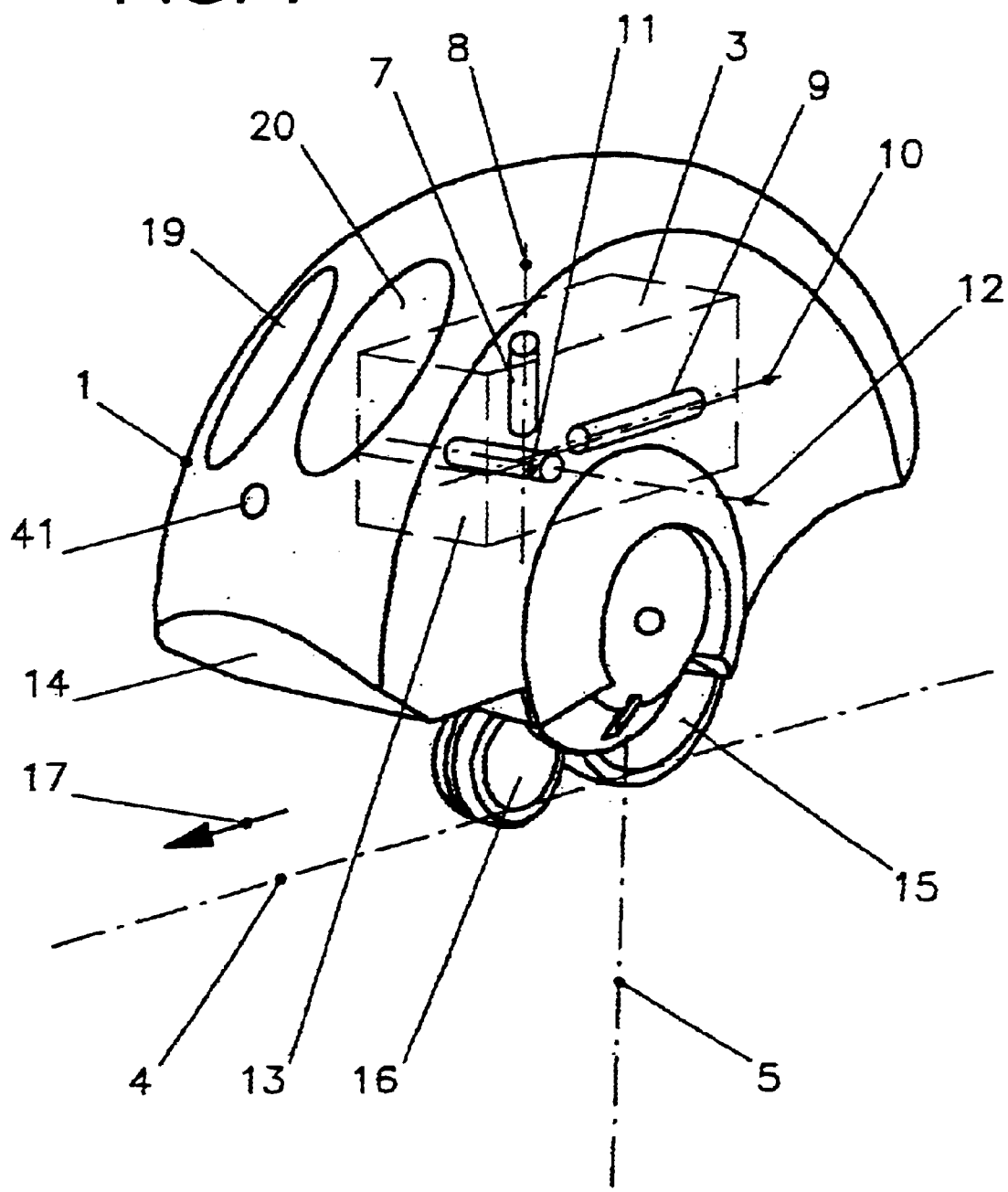

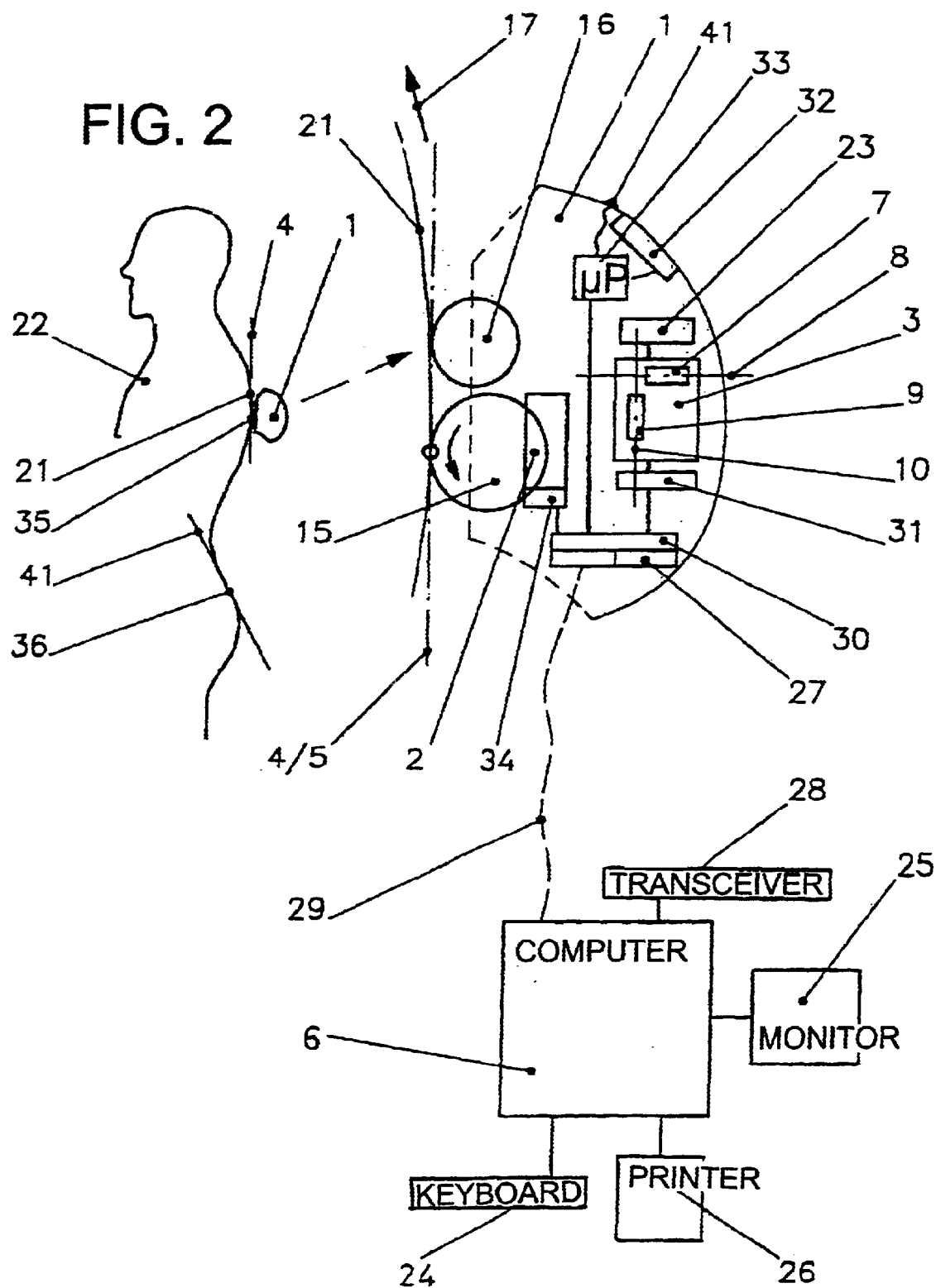

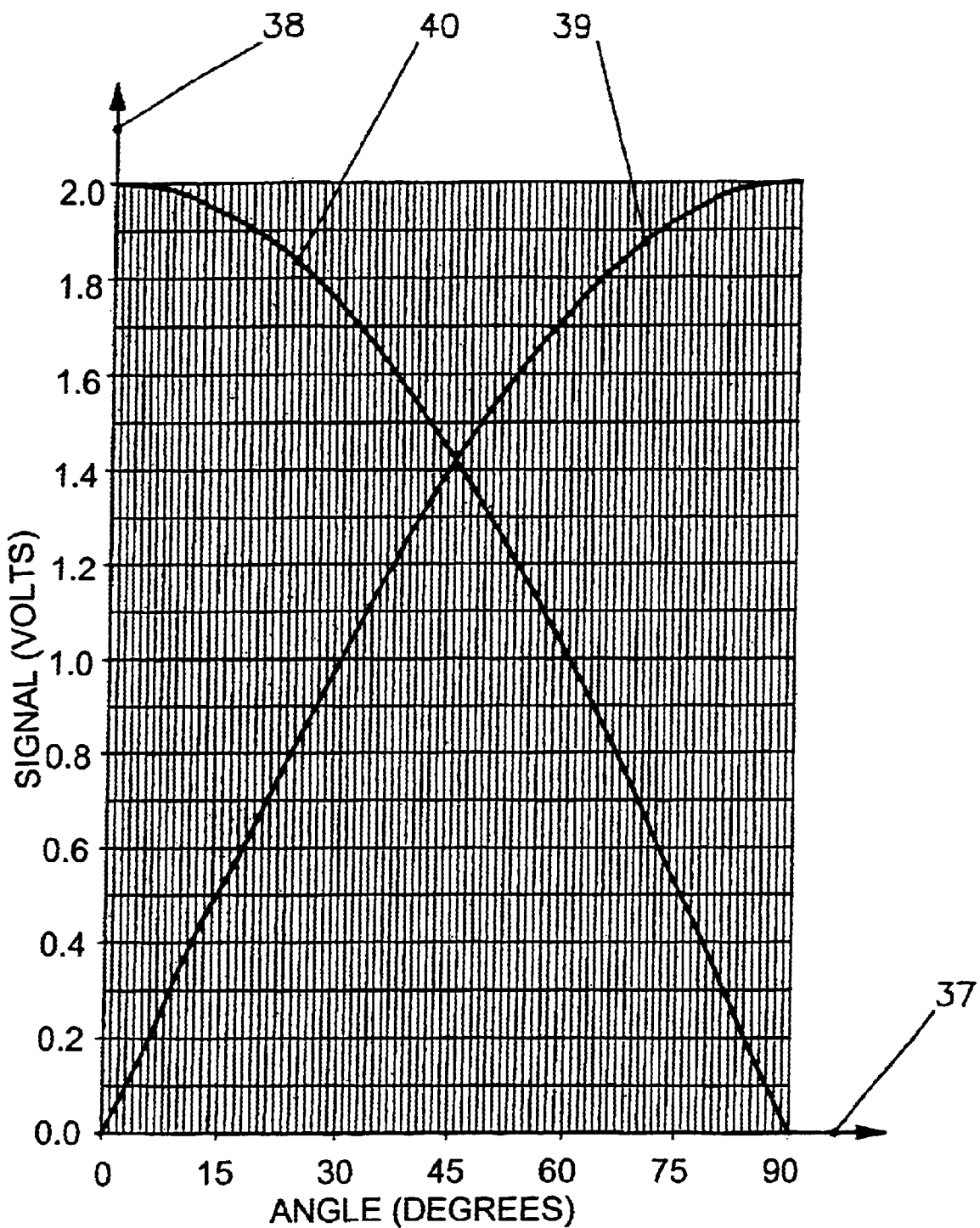

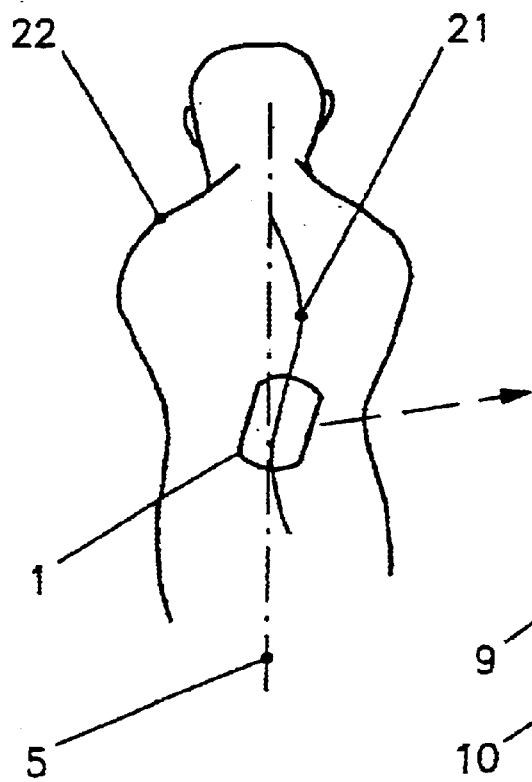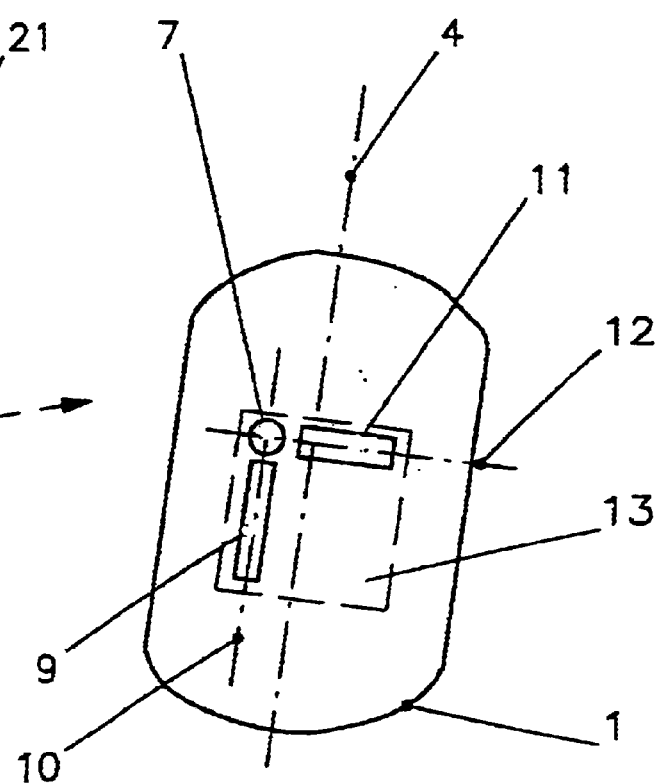

MEASURING SYSTEM FOR DETERMINING THE SURFACE LINE OF A BODY

FIELD AND BACKGROUND OF THE INVENTION

The invention relates to a measuring system for determining the shape and length of a surface line of a body with a freely movable measuring instrument, which is equipped with a measuring device for measuring the length of a displacement path of the measuring instrument along the surface line and a measuring device for determining angular changes of a measuring axis of the measuring instrument with respect to a predetermined reference axis, with a data transfer device to a computer and a computer which processes the path and angle measurements of the two measuring instruments and generates a representation of the surface line.

Such measuring systems are in particular applied for acquiring and scanning the shape and length of body contours and of ranges of motion in the case of articulated bodies, in particular human bodies. Of particular interest are the acquisition of the shape and length of the course of the vertebral column and measuring for checking its mobility, but also for measuring the course of motions on other joints, such as, for example, hip or knee joints. A measuring system of this type is known, for example, from DE 40 90 228 C1, in which different application feasibilities in the area of measurements on the vertebral column are also described. In this known system, a freely movable measuring instrument is available, which is:connected to a computer for evaluating and representing the data. In the movable measuring instrument a measuring device is available for measuring the length of the displacement path of the measuring instrument, and specifically an electric path-measuring sensing element. This path measuring device includes rollers or cylinders, which, during the displacement of the measuring instrument, track along the surface or line to be measured and means, known per se, for converting this tracking motion into electric signals, for example via an incremental displacement transducer. The measuring instrument further includes also an angle measuring device in the form of a vertical pendulum device. This vertical pendulum device is developed such that it can be applied in two positions pivoted by 90°. This allows in a first measuring process by tracing the surface line with the movable measuring instrument determining curvatures in one direction and by repeating the tracing process and resetting the vertical pendulum device by 90°, curvatures of the surface line in a plane at right angles to [the first plane]. To determine the curvature and shape of the surface line, at specific points, or intervals of the path of this surface line, the corresponding angular deviations via the vertical pendulum and on that basis to determine the curvature of the surface line. The vertical pendulums applied for angle measurements represent relatively sensitive, and also correspondingly expensive, measuring instruments, and, in the commercially available implementations, they also have only a limited angle measuring range. If, in the case of measurements on the human body, for example in patients with back complaints, measurements must be carried out on the standing and also on the lying body, these different measurements require a resetting of the measuring instrument, for example of the vertical pendulum device, for the particular position of the patient. As a consequence, the measuring electronics must also be newly initiated and the originating point of the measurement must be started accordingly. This is time consuming and can also lead to discrepancies of the measuring results and to errors, since movements in the interim by the patient cannot be excluded.

A further measuring system for acquiring the back contour of a human being is known from DE 44 02 562 A1. In this system a vertical pendulum is also applied for angle measurements in the movable measuring instrument. While this vertical pendulum has an increased angle measuring range, it entails, however, additionally the disadvantage that vertical pendulums are sensitive measuring instruments with a complicated interior structure. They are therefore correspondingly expensive and also require careful handling and correct application. During the measurements the vertical pendulum must be oriented as must as feasible in a vertical plane since otherwise the damping could falsify the measurement results. With too great a deviation from the vertical plane, measurements can even become impossible.

In practice difficulties are therefore repeatedly encountered since the measured object on which the shape and length of a surface line is to be acquired, must be moved into a position which corresponds to the permissible measuring range of the measuring system. In particular in the case of measurements on the human body and wherever measurements or sequences of measuring series must be carried out rapidly, this makes the course of measurement difficult. The known measuring systems therefore require corresponding training and practice in the application. Even with correspondingly trained operators the time expenditure for carrying out measurements is, to some extent, still considerable, and, in particular, resetting the angle measuring device and the respective initialization are time-consuming.

SUMMARY OF THE INVENTION

The objective of the present invention is to provide a measuring system or a measuring instrument, with which the acquisition of shape and length of surface lines of a body in a plane over an angular range from 0 to 360° is possible, with changes of position of the measuring instrument or with changing measuring processes no initialization and calibration of the measuring instrument is necessary, the measuring device for determining the angular changes in [three-dimensional] space is structured simple and freely movable, and the course of the surface line in the same measuring process can be determined with respect to two measuring surfaces, oriented at right angles to one another, or as a space vector.

This object is attained through the features defined in the claims to and forming part of this application.

In the measuring system according to the invention the movable measuring instrument is equipped with a measuring device, known per se, for measuring the length of a displacement path along a surface line, as is described in prior art. In combination with this length measuring device, known per se, the measuring device for determining angular changes of a measuring axis of the measuring instrument, is developed with two acceleration sensors. Application of acceleration sensors for determining angular changes of the measuring device yields the advantage that sensors can be employed which have a precisely defined measuring axis and, additionally, no movable parts exist which must be supported such that they are pivotable about an axis or are equipped with damping elements. This significantly simplifies the structure of the measuring device for determining angular changes and the susceptibility to malfunction is considerably reduced. The acceleration sensors proposed for use, are sensors which normally are applied to determine accelerations and decelerations of moving objects in the direction of their measuring axis. But such sensors, known per se, also have the property that even in the stationary state, i.e. without a motion component in the direction of their measuring axis, they output measuring signals with angular changes of the measuring axis. This effect can be traced back to the normal gravitational force, or acceleration due to gravity, which always acts on the sensor. If an acceleration sensor is oriented such that the measuring axis is parallel to the gravitational axis, the full acceleration due to gravity acts on the measuring element of the acceleration sensor. If the measuring axis of the acceleration sensor is precisely at right angles to the gravitational axis, the measuring element of the acceleration sensor is not deflected and no component of the acceleration due to gravity acts in the direction of the measuring axis. Depending on the angular position between 0 and 90°, the acceleration sensor generates different measuring signals, from which the angular position of the measuring axis of the acceleration sensor relative to the gravitational axis can be derived. Known acceleration sensors comprise a sensor and an integrated circuit which is normally developed as a closed unit with a power connection and a signal output. However, the dependence of the signals output by the acceleration sensor is not a linear function of the angle but rather the sensitivity in the proximity of 90° with respect to the gravitational axis is greatest and in the range, in which the measuring axis is moved into a parallel position with the gravitational axis, it is low.

A further advantage is obtained if in one measuring plane two acceleration sensors are disposed whose measuring axes lie in this common plane and are disposed at right angles to one another. If the output signals of these two acceleration sensors are linked, a unique assignment to a specific angle relative to the gravitational axis is obtained and simultaneously high precision since one of the two sensors is always effective in the range of high sensitivity. Since the two acceleration sensors are not dependent on a rotational axis, but their measuring axis can fundamentally be disposed in any desired manner in space, the advantage is obtained that the plane in which the two measuring axes of the acceleration sensors are disposed, can be oriented in the measuring instrument such that the measuring axis of the measuring device for the displacement path is also in this common plane. The output signals of the acceleration sensors are conducted to a transducer and such is connected across an interface and a data line with a computer, advantageously a personal computer. This data line can be formed by a cable, and an especially advantageous solution is obtained if the data of the transducer can be transferred wirelessly to the computer. This increases the free mobility of the measuring instrument, and it is readily handlable by the operating personnel.

By using a third acceleration sensor, in simple and advantageous manner a second measuring device for determining angular changes can be formed, thereby that this third acceleration sensor is combined with one of the two sensors of the first measuring device for determining angular changes, to form a second measuring device. The measuring axis of this third acceleration sensor is disposed in a plane which is at right angles to the plane formed by the measuring axes of the two first acceleration sensors. Thereby that two sensors each are combined to form a first and a second measuring device, angular changes can be detected in two planes perpendicular to one another. The measuring range extends from 0 to 360° in each of the two planes since one of the sensors is always within the sensitive measuring range. Since the characteristic of the signal curve as a function of the angle of the measuring axis to the gravitational axis is known precisely, the angles can be determined with high precision and over the entire range. The measuring system according to the invention offers additionally the advantage that different models of acceleration sensors can be employed since their signal or measuring characteristic is known from the outset. Through the appropriate evaluation of the measuring signals in the computer with suitable software any desired angle in space in the X- as well as the Y- and the Z-axis can be determined. If needed, these measuring signals can also be converted into vectors. In connection with the measured values from the path measurement, the measured values from the angle measurement are used to represent the course of surface lines of a body.

To acquire the shape and length of a surface line of a body, for example the shape of the vertebral column of a human being, the measuring instrument is moved along the vertebral column or the surface line. The measuring device for measuring the length of the displacement path senses the corresponding displacement movement and, via the transducer, the corresponding measured values are transferred as data to the computer. At predetermined path and/or time intervals for this purpose, via the measuring devices for determining angular changes, the angles of inclination of the surface line are determined. From the data belonging to a specific measuring point the course of the surface line in the region of this measuring point is calculated and subsequently, based on the multiplicity of measuring points, the course of the total curve or the total surface line is determined. Such can subsequently, in a manner known per se, be represented or output on an output apparatus, such as a printer or a monitor, and can be made accessible to a viewer. During a movement process of the measuring instrument, intermediate states of the curve of the movement and final states can be determined and represented. The measuring system according to the invention does not require calibration in the starting position since, due to the measurement values of the sensors, it is always possible to determine precisely which positions are assumed by the measuring axes of the measuring instrument with respect to the gravitational axis. This facilitates considerably the course of measuring processes, for example on patients with back or joint complaints, since these are not forced to assume a specific measuring position. For standard measurements it is certainly useful to start from at least one or several approximate normal positions. This facilitates the comparison of measuring processes with one another and also the evaluation of the displayed results. With sufficient experience of the operating personnel and the use of suitable software, the measuring system according to the invention also makes possible measurements in any position, i.e. the application range of this measuring system is considerably expanded. In spite of this expansion of the application range, the measuring instrument is easy to handle and not subject to malfunctions.

Disposing an input apparatus with at least one control key on the movable measuring instrument offers the further advantage that the operatability is improved thereby that control functions for the data processing in the PC can be actuated via these control keys and, for example during the measuring processes, the control keyboard proper of the computer is replaced by these control keys. Facilitation of the work resulting therefrom is considerable and permits working fast and precisely. A further improvement is obtained by disposing a display arrangement on the measuring instrument. This display arrangement can be formed by a light-emitting. diode (LED) or by another arrangement, known per se, such as a liquid crystal display (LCD). A light-emitting diode could visually display certain operating states. When using a liquid crystal display the expanded capability is obtained for displays in the form of symbols, numerals or text. This display arrangement makes it possible for the operating personnel to direct their entire attention to the measuring process and the measuring instrument since all operation messages can be displayed on the measuring instrument. This also contributes to additional ease and acceleration of the measuring process.

BRIEF DESCRIPTION OF THE DRAWINGS

In the following the invention will be described in further detail with the aid of drawings which represent embodiment example. Therein depict:

FIG. 1 a perspective view of a measuring instrument of the measuring system according to the invention, FIG. 2 the measuring system according to the invention in schematic representation, FIG. 3 a diagram with the output signals of a sensor pair as a function of the measuring angle;

FIG. 4 a schematic representation of a measuring position at right angles to the measuring plane shown in FIG. 2; and FIG. 5 shows the measuring instrument of FIG. 4 on an enlarged scale.

DESCRIPTION OF THE PREFERRED EMBODIMENTS

FIG. 1 shows a freely movable measuring instrument 1 according to the invention. This measuring instrument 1 comprises an ergonomically formed housing 14, which can be held simply and comfortably in one hand. In the housing 14 is supported a measuring wheel 15 and a guide wheel 16. The guide wheel 16 and the measuring wheel 15 are oriented toward a guide axis 4 and are parts of a measuring device 2 (see FIG. 2) for measuring the length of displacement paths of the measuring instrument 1 along the measuring axis 4 in the direction of arrow 17. The measuring instrument 1, furthermore, comprises two keys 19, 20 which are a component of an input apparatus 32 depicted in FIG. 2. In housing 14 of the measuring instrument 1 are disposed, additionally, a first measuring device 3 and a second measuring device 13 for measuring angular deviations of the measuring instrument 1, or of the measuring axis 4 with respect to a reference axis 5. Both measuring devices 3 and 13 are therein indicated only schematically. The reference axis-5 is formed by the axis of the direction of the acceleration due to gravity, i.e. by the gravitational axis and is therefore in each case defined and given. The first measuring device 3 for determining angular changes of the measuring axis 4 comprises a first acceleration sensor 7 with a measuring axis 8 and a second acceleration sensor 9 with a measuring axis 10. Both measuring axes 8 and 10 of the two acceleration sensors 7 and 9 are in a common plane and are disposed at right angles to one another. The measuring axis 10 of the acceleration sensor 9 in the position of the measuring instrument 1 shown in FIG. 1 is at right angles to reference axis 5 and the measuring axis 8 of the acceleration sensor 7 extends parallel to it. The measuring device 3, which comprises the two acceleration sensors 7 and 9, is installed in housing 14 of the measuring instrument 1 such that the measuring plane, defined by the two axes 8 and 10, extends parallel to the measuring axis 4 of the measuring device 2 for length measurement or this measuring axis 4 is in the same plane. With this first measuring device 3 for determining angular changes, angular changes of the measuring instrument 1 relative to the reference axis 5 are determined which occur during rotations of the measuring instrument 1 in the plane formed by the measuring axis 4 and the reference axis 5. With the second acceleration sensor 9 and a third acceleration sensor 11 a second measuring device 13 for angular changes is developed, with the measuring axes 10 and 12 of these two acceleration sensors 9 and 11 also being at right angles to one another and defining a measuring plane which is at right angles to that in which lie the two measuring axes 8 and 10 of the acceleration sensors 7 and 9 of the first measuring device 3 for angular changes. This second measuring device 13 for angular changes is used in particular when the measuring instrument 1 is applied in an approximately vertical position, i.e. if the measuring axis 4 for the length measurement extends approximately in the direction of reference axis 5. The acceleration sensors 7, 9 and 11 are commercially available electronic components, integrated into an electronic circuit. Each of the three acceleration sensors 7, 9 and 11 is capable of functioning by itself and for that purpose is provided with an energy supply, or a power connection and a signal output. The combination of two acceleration sensors 7, 9 or 9, 11 each to form a measuring device 3, or 13, for angular changes, permits precise angle measurements from 0 to 360° in the planes defined by the measuring axes 8, 10 or 10, 12, respectively. The system according to the invention of three acceleration sensors 7, 9, 11 therefore makes possible the simultaneous measurement of angular changes in two vertical planes perpendicular to one another or of two angular positions of the measuring instrument 1 with respect to the reference axis 5. These angle values can be assigned to certain positions of a surface line 21 (according to FIG. 2) which are determined by the measuring device 2 for measuring the length of the surface line 21. As described in the following, from these data the shape of a curve in [three-dimensional] space, for example the surface line 21, can be determined. The measuring instrument 1 is additionally equipped with a light-emitting diode (LED) 41, which forms a display arrangement or an output apparatus for visual information. By the condition bright or dark and/or by different color displays, for example red/green, certain states of the measuring process can be displayed. If needed, the LED can also be replaced by a liquid crystal display. This makes possible the display, or output, of more extensive information, for example texts or symbols.

In FIG. 2 is schematically shown the measuring system for acquiring the shape and length of a surface line 21 of a body 22. In the example depicted, the measuring instrument 1 is used for the purpose of determining on a human body 22 the length and shape of the vertebral column, i.e. its surface line 21 in a sagittal plane. The body 22 is depicted in the standing position, but can also be in a stooped or lying position. In the right portion of FIG. 2 the measuring instrument 1 is shown schematically and enlarged. The measuring instrument 1 is connected with a computer 6 which, with the aid of a suitable software, processes the measurement data determined by measuring instrument 1 and generates a representation of the surface line 21 of the vertebral column of body 22. Computer 6 is connected, in a manner known per se, with an input apparatus in the form of a keyboard 24, with a monitor 25, a printer 26 and potential further hardware elements. In the example represented in FIG. 2 for the transfer of the data between the measuring instrument 1 and the computer 6 a device for the wireless transmission of data is provided. For this purpose on measuring instrument 1 and on computer 6 each a transmitting/receiving unit 27 or 28 is disposed which, in known manner is suitable for data transmission, for example by means of radio or infrared signals. As indicated by the dot-dash line 29 a cable can also be employed as the data line. However, this reduces the free movability of the measuring instrument 1. Measuring instrument 1 is equipped with an interface 30, with which all measuring devices 2, 3 and 13 of the measuring instrument 1 are connected across data lines. To measure the displacement path of the measuring instrument 1 in the direction of arrow 17 along the surface line 21, the measuring instrument 1 is equipped with the measuring device 2 for the length measurement. With displacements of the measuring instrument 1 in the direction of arrow 17 the measuring wheel 15 tracks along the surface of body 22. The rotational movement of the measuring wheel 15 about an axis resulting therefrom is acquired incrementally and the corresponding data are supplied to the interface 30 across a transducer 34. Furthermore, an input apparatus 32 with at least one control key, preferably two control keys 19, 20 is available which is linked to a microprocessor 33. In the example shown, this microprocessor 33 is equipped with a data store as well as an input/output unit, wherein the data store makes possible the intermediate storage of path and angle measurement data. Access to these data is possible through the input apparatus 32 on measuring instrument 1 or through an input apparatus of computer 6, for example via the keyboard 24. The microprocessor 33, or its input/output unit includes a switching element which assigns the control optionally to the input apparatus 32 on measuring instrument 1 or to the input apparatus, or keyboard, on computer 6. The corresponding switching element can also be disposed on a processor in computer 6. Via the input/output unit of microprocessor 33 the visual display arrangement 41 is also controlled. In the example shown, this is a light-emitting diode which displays certain operating states of the measuring process through different colors and the states by emitting or not emitting light. Readiness to start the measurement is, for example, displayed by green and emission of light. It can also be useful to arrange several light-emitting diodes and to connected them through the microprocessor 33. An energy source 23 which comprises a battery or a rechargeable accumulator, serves for supplying the measuring device 2 for the length measurement and the measuring devices 3 and 13 for the measurement of angular changes, as well as potential further electric components. The measuring devices 3 and 13 for determining angular changes are also connected with a transducer 31, which, in turn, is linked with the interface 30. The first measuring device 3, shown in principle in FIG. 2, for determining angular changes or angular positions of the measuring instrument 1 comprises the two acceleration sensors 7 and 9.

The acceleration sensors 7, 9, 11 employed in this example are sensors of a type known per se and are conventionally employed for the purpose of determining accelerations or decelerations in the direction of their measuring axes 8, 10, 12. In the measuring instrument 1 according to the invention the property of such acceleration sensors 7, 9, 11 is utilized that even in the stationary state, i.e. without a motion component in the direction of their measuring axes 8, 10, 12, they generate measuring signals upon changes of the position of the measuring axes 8, 10, 12 with respect to the axis 5 of the acceleration due to gravity. The acceleration or deceleration forces acting through the movement of the measuring instrument 1 along the surface line 21 onto the sensors, can therein be neglected since they do not cause any change of the signals given the speeds of movement occurring here. The acceleration sensors 7, 9, 11 have the advantage that they generate positive or negative signals depending on the direction of change of the angle relative to the gravitational axis 5. Therewith the direction of the angular deviation can be determined. With the normally available acceleration sensors 7, 9, 11 the characteristic which indicates the relationship of the input variable to the output variable, is not linear. In the configuration of sensors 7 and 9 provided in-the measuring device 3, their measuring axes 8 or 10 are at right angles to one another. In the position shown in FIG. 2, the two measuring axes 8 and 10 define a measuring plane which corresponds to the plane of the drawing. If the measuring instrument 1, during its displacement along the surface line 21, is tilted in this plane such that the angle of the two measuring axes 8 and 10 of acceleration sensors 7 and 9 relative to the reference axis, or gravitational axis, 5, sensors 7 and 9 generate measuring signals which yield the characteristic shown in FIG. 3 as a function of the angular position.

In the diagram shown in FIG. 3, in the direction of axis 37 the angular changes of the measuring axes 8 or 10 are plotted in relationship to reference axis 5 and on the axis 38, at right angles to it, the measuring signals, for example, as voltage values. Curve 39 represents the characteristic for acceleration sensor 7 and curve 40 the characteristic for acceleration sensor 9. Based on this characteristic diagram it is evident that acceleration sensor 7 has very good resolution in the range of angular changes from 0° to approximately 60°. In the range up toward 90°, however, the resolution becomes increasingly poorer, i.e. the measurement result is imprecise. In contrast, the characteristic of acceleration sensor 9 shows, that its signals yield in the range from 0° to approximately 30° poor resolution, i.e. an imprecision of the measurement results, and starting at approximately 30° to 90° the resolution is very good and thus also the measuring precision is very high. Nevertheless, in order to be able to carry out precise measurements in the entire range from 0 to 360°, the two acceleration sensors 8 and 9 form a pair of measuring elements, and for each angular position, the signals of both sensors 8, 9 are acquired. The measuring signal, or measurement value pair resulting therefrom, permits the precise assignment to a certain angle and specifically over the entire range from 0 to 360°. In the position, shown in FIG. 2, of the measuring instrument 1, which is, assigned to measuring point 35 on surface line 21, for the acceleration sensor 7 a measurement value is obtained of 0 and for acceleration sensor 9 a measurement value of +2. This uniquely defines that the measuring instrument 1 is in the vertical position and the guide wheel 16 is directed upwardly. If the measuring instrument 1 were to be rotated by 180°, i.e. if the guide wheel 16 were directed downwardly, the acceleration sensor 7 would still output a measurement value of 0, however, the acceleration sensor 9 a measurement value of −2. The processing of these measurement value data in the measuring system according to the invention is carried out in computer 6 with the aid of corresponding software. But processing can to some extent also take place in microprocessor 33, and, in this case, correspondingly processed data are transferred further to computer 6. For measuring point 36 on surface line 21 of body 22, the measuring axis 4' of the measuring instrument 1 would have an angular deviation with respect to the reference axis 5 when the measuring wheel 15 as well as also the guide wheel 16 rest property on surface line 21. In this position sensor 7 would output a measurement value of 0.96 and sensor 9 a measurement value of 1.75. This measurement value pair only occurs at an angle of +30° and, for that reason, the position of the measuring instrument 1, or the position of the measuring axis 4, 4', can be precisely determined. This applies to any point on the surface line 21 with the body 22 in the standing position as well as also when bending or lying down.

The measuring system according to the invention permits simultaneously with the measurement of shape and length of the surface line 21 in the sagittal plane, i.e. In a plane parallel to the plane of the drawing of FIG. 2, the acquisition of the shape of the surface line 21 in frontal planes at right angles to it. As shown in FIG. 4, the measuring instrument 1 is for this purpose equipped with a second measuring device 13 for determining angular deviations. This measuring device 13 comprises the acceleration sensor 9, which simultaneously belongs to the first angle measuring device 3 and, additionally, a third acceleration sensor 11. The measuring axis 12 of this third acceleration sensor 11 is disposed perpendicularly with respect to measuring axis 10 of acceleration sensor 9 and to the measuring axis 8 of acceleration sensor 7. Both measuring axes 10 and 12 of the two acceleration sensors 9 and 11 of measuring device 13 define a measuring plane which extends at right angles to the measuring plane of measuring device 3. This measuring plane determined by the two measuring axes 10 and 12, in the example shown corresponds to the plane of drawing of FIG. 4. If the measuring instrument 1 is displaced along surface line 21, the measuring device 2 for determining the length or segments of the distance, generates, on the one hand, corresponding measurement data and to each measuring position are output from the measuring device 13 corresponding measurement data for determining the angles. As already described in connection with FIGS. 2 and 3, the measurement signals of both acceleration sensors 9 and 11 are combined correspondingly to form measurement value pairs which permit the unique determination of the angle of the measuring axis 4 of measuring instrument 1 with respect to the reference axis, or gravitational axis, 5 in a frontal plane. These measurement data are, in turn, processed with the corresponding software in computer 6 and the shape of surface line 21, i.e. In the example described, the curvature of the vertebral column in the frontal plane (scoliosis) is reproduced.

FIG. 5 shows the instrument of FIG. 4 on an enlarged scale.

To measure the course and the shape of the surface line 21 in a sagittal or frontal plane, the measurement data are normally sufficient, which are determined by the first or second measuring device 3 or 13 for determining angular deviations. In the event of large angular deviations in both planes it may, however, be necessary to take into consideration and to compensate the deflection of the measuring planes from the ideal vertical plane. This is possible in the system according to the invention of the two measuring devices 3 and 13, since in each instance measurement signals of a third acceleration sensor 11 or 7 are available, which indicate deflections in a plane at right angles to the measuring plane. The measurement data generated by this third measuring sensor 11 or 7 are utilized for correcting the measurement value pair data of the two other acceleration sensors 7 and 9, or 9 and 11. The corresponding system according to the invention of the three acceleration sensors 7, 9, 11 can be installed in simple manner into the measuring instrument 1, it is cost-effective and has low susceptibility to malfunction. It is also possible to employ acceleration sensors 7, 9, 11 with different measurement characteristics wherein the course of the characteristics can be developed within a wide range between linear and nonlinear. The measuring device 2 for measuring the length of the displacement path along the surface curve 21, as well as also the two measuring instrument 3 and 13 for measuring the angular changes, can be laid out small and compactly such that the measuring instrument 1 can be developed to be very light and readily handlable. In particular when using wireless transmission of data between the measuring instrument 1 and the computer 6 very good handlability and operatability of the measuring system results. Due to the configuration of control elements in the form of the input apparatus 32 with the control keys 19 and 20 as well as the display arrangement 41 on measuring instrument 1 this facilitated operatability is additionally increased. The corresponding measurements can be completed more rapidly and more simply. This not only applies to measuring the shape and length of the vertebral column but also for measuring the shape and also the mobility of other joints of the human body 22 or of other objects.

What is claimed is:

1. A measuring system for acquiring shape and length of a surface line (21) of a body (22) in space, comprising: a freely movable measuring instrument (1) with a length measuring device (2) for measuring the length of a displacement path of the measuring instrument (1) along the surface line (21) and a further measuring device (3) for determining angular changes of a measuring axis (4) of the measuring instrument (1) with respect to a selected reference axis (5); a data transmission device for transmitting data to a computer (6); a computer (6) for processing path and angle measurement values of the measuring devices (2, 3) and for generating a representation of the surface line (21); the length measuring device (2) for the displacement path comprising a measuring wheel (15) and guide means (16) which are spaced from each other and form two contact points with the surface (21), the contact points being on the measuring axis; the further measuring device (3) for determining angular changes comprising two acceleration sensors (7, 9) with one measuring axis (8, 10) each, the measuring axes (8, 10) of the two acceleration sensors (7, 9) being in a common plane and the two measuring axes (8, 10) being at right angles to one another in the common plane and the measuring axis (4) of the length measuring device (2) for the displacement also being in the common plane.

2. A measuring system as claimed in claim 1, including, in addition to the further measuring device (3) which comprises a first measuring device, with the two acceleration sensors (7, 9) for determining angular changes which comprise first and second acceleration sensors; a second measuring device (13) for determining angular changes, the second measuring device (13) comprising a third acceleration sensor (11) and including one of the first and second acceleration sensors (7, 9) of the first measuring device (3), and a measuring axis (12) of the third sensor (11), being at right angles to the plane of the measuring axes (8, 10) of each of the two sensors (7, 9) of the first measuring device (3).

3. A measuring system as claimed in claim 2, wherein each of the acceleration sensors (7, 9, 11) is connected to an energy source (23) and to a transducer (31) and the transducer (31) is connected to the computer (6) across an interface (30) and a data line (29; 27, 28).

4. A measuring system as claimed in claim 1, wherein the reference axis (5) for determining the angular deviations is a vertical axis determined by the direction of acceleration due to gravity.

5. A measuring system as claimed in claim 1, wherein the measuring device (2) for the displacement path is connected to a transducer (34) and the transducer (34) is connected across an interface (30) and a data line (29; 27, 28) to the computer (6).

6. A measuring system as claimed in claim 1, wherein the measuring wheel (15) includes a device for converting length values into digital electric signals.

7. A measuring system as claimed in claim 1, wherein the freely movable measuring instrument (1) includes an input apparatus (32) with at least one control key (19, 20), a microprocessor (33) connected therewith and a data line (29; 27, 28) to the computer (6).

8. A measuring system as claimed in claim 1, wherein the connection between the freely movable measuring instrument (1) and the computer (6) comprises devices for wireless transmission of data, whereby the freely movable measuring instrument (1) and the computer (6) each comprise a transmitting/receiving unit (27, 28), and all data lines in the measuring instrument (1) being connected to the transmitting/receiving unit (27).

9. A measuring system as claimed in claim 1, wherein the measuring instrument (1) or the computer (6) is equipped with a microprocessor (33) in the form of an input/output unit and the microprocessor (33) is a switching element between an input apparatus (22) on the measuring instrument (1) and an input apparatus (24) on the computer (6).

10. A measuring system as claimed in claim 1, wherein the measuring instrument (1) comprises a visual display arrangement (41).

11. A measuring system as claimed in claim 10, wherein the visual display arrangement (41) comprises at least one light-emitting diode or a liquid crystal display.

* * * * *